US012622473B2

(12) United States Patent
Zhai

(10) Patent No.: US 12,622,473 B2
(45) Date of Patent: May 12, 2026

(54) ANTIVIRAL ELECTROSPUN FIBERS AND METHODS OF REDUCING AIRBORNE PATHOGEN SPREAD

(71) Applicant: University of Central Florida Research Foundation, Inc., Orlando, FL (US)

(72) Inventor: Lei Zhai, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 521 days.

(21) Appl. No.: 17/575,102

(22) Filed: Jan. 13, 2022

(65) Prior Publication Data

US 2022/0218053 A1     Jul. 14, 2022

Related U.S. Application Data

(60) Provisional application No. 63/199,623, filed on Jan. 13, 2021.

(51) Int. Cl.
*A41D 13/11*          (2006.01)
*A61L 9/00*          (2006.01)
(Continued)

(52) U.S. Cl.
CPC ............ *A41D 13/1192* (2013.01); *A61L 9/00* (2013.01); *D04H 1/728* (2013.01);
(Continued)

(58) Field of Classification Search
CPC ............. D06M 15/53; D06M 2101/28; D06M 2101/40; D06M 2200/30; D01F 9/22;
(Continued)

(56) References Cited

U.S. PATENT DOCUMENTS

2009/0320849 A1 * 12/2009 Biedermann ....... D06M 15/263
128/206.28

FOREIGN PATENT DOCUMENTS

WO     WO-2008049397 A2 *  5/2008  ........... D01D 5/0038
WO        2010067873 A1   6/2010

OTHER PUBLICATIONS

Bai, Bingyu, "Electrospun Chitosan Nanofiber for Virus Removal," Michigan Technological University, 2012. (Year: 2012).*
Lu. Polyelectrolyte Complexes Based on Poly(acrylic acid): Mechanics and Applications. Electronic Theses and Dissertations. University of Central Florida. 2018: 5769.
(Continued)

*Primary Examiner* — Matthew D Matzek
(74) *Attorney, Agent, or Firm* — Molly L. Sauter; Trenam Law

(57) ABSTRACT

Methods of forming an antiviral facial mask that is capable of not only filtering pathogen particles, but also deactivating pathogen particles prior to exposure by the wearer. Typical facial masks do not deactivate pathogen particles, but rather merely capture viral particles on an outer surface of the mask. As such, the masks present a risk of interaction between the mask wearer and the particles, such as during the removal and/or application of the masks. Methods of forming enhanced antiviral facial masks include the formation of fibers via electrospinning, such that the fibers include a solution of two oppositely charged polyelectrolytes, surfactants, and metal ions. In use, water from human breath activates the surfactants to capture and deactivate pathogen particles. Moreover, the strength of the fibers from the oppositely charged polyelectrolytes results in increased lifespans of the masks, as the masks do not breakdown in the presence of high humidity.

4 Claims, 5 Drawing Sheets

(51) Int. Cl.

| | |
|---|---|
| *D04H 1/728* | (2012.01) |
| *A61L 101/32* | (2006.01) |
| *A61L 101/46* | (2006.01) |
| *A61L 101/50* | (2006.01) |

(52) U.S. Cl.

CPC ....... *A61L 2101/32* (2020.08); *A61L 2101/46* (2020.08); *A61L 2101/50* (2020.08); *A61L 2209/14* (2013.01); *D10B 2501/042* (2013.01)

(58) Field of Classification Search

CPC .......... D04H 1/4242; D04H 1/43; D04H 1/74; D04H 3/002; D04H 3/007; D04H 3/02; D04H 1/728; D10B 2101/12; D10B 2401/04; D10B 2501/042; A41D 13/1192; A61L 9/00; A61L 2101/32; A61L 2101/46; A61L 2101/50; A61L 2209/14; A61L 2/238; A61L 9/16; A61L 2/232

USPC ......... 442/123, 327; 977/762, 832, 836, 904

See application file for complete search history.

(56) References Cited

OTHER PUBLICATIONS

Jarach et al., Polymers in the Medical Antiviral Front-Line Polymers. Polymers. 2020. vol. 12: 1727.

Quan et al., Universal and reusable virus deactivation system for respiratory protection. Scientific Reports. 2017. vol. 7: 39956.

Malhotra et al., Bioinspired Metal Ion Coordinated Polyelectrolyte Fibrous Nanoreactors. Adv. Mater. Interfaces. 2016. vol. 3: 1600692.

Translation of WO2010/067873 A1 with a publication date of Jun. 17, 2010; Applicants: Hiroshima University and Altan Co., LTD.

* cited by examiner

Mag = 5.00 K X    EHT = 5.00 KV

Signal A = SE2    WD = 6.1 mm

1 μm

Mag = 15.00 K X    EHT = 5.00 kV

Signal A = SE2    WD = 6.1 mm

1 µm

10

Provide two polyelectrolytes having opposite charges

12

Mix the two polyelectrolytes to form a solution

14

Before electrospinning, add an amount of surfactant molecules and an amount of metal ion molecules to the solution

16

Electrospin the solution to form one or more fiber strands

18

Form the electrospun surfactant-infused fibers into a nonwoven facial mask

ANTIVIRAL ELECTROSPUN FIBERS AND METHODS OF REDUCING AIRBORNE PATHOGEN SPREAD

CROSS-REFERENCE TO RELATED APPLICATIONS

This nonprovisional application claims priority to provisional application No. 63/199,623, entitled "Antiviral electrospun fibers and methods of reducing airborne pathogen spread," filed on Jan. 13, 2021 by the same inventor, the entirety of which is incorporated herein by reference.

BACKGROUND OF THE INVENTION

1. Field of the Invention

This invention relates, generally, to antiviral fibers, such as those nonwoven into masks. More specifically, it relates to antiviral electrospun fibers infused with one or more surfactants and metal ions that can be used to reduce the spread of airborne pathogens, such as those associated with severe acute respiratory coronavirus 2 (SARS-CoV-2) and similar infectious diseases.

2. Brief Description of the Prior Art

Airborne transmitted pathogens, including SARS-CoV-2 and similar infectious diseases, often spread through close contact between humans. Whether the spread is through direct host-to-host transmission or through surface-to-host transmission, the transmission path is similar—droplets carrying the pathogen are transmitted from one host through natural human respiratory functions, including breathing, speaking, sneezing, and coughing. The secondary host merely needs to contact the droplets through his or her respiratory system (either directly, such as through breathing, or indirectly, such as through a secondary transmission via a hand-to-surface contact) to be exposed to the pathogen.

As such, some of the most widespread and effective methods of preventing or reducing pathogen transmission depend on decreasing the likelihood of exposure to airborne pathogens. Efforts to reduce close contact between humans, generally termed "social distancing," include the physical spacing apart of occupants of a given space to reduce overlaps in respiratory functions, as well as reductions in attendance capacities for given spaces, particularly indoor spaces with centralized airflow systems. By reducing the opportunities for people to interact in an enclosed space, the likelihood of pathogen transmission decreases.

Similarly, widespread adoption of facial masks and shields has proven to be effective at reducing transmission rates. By wearing a facial mask, the wearer reduces the likelihood of pathogen transmission both into and out of the wearer, since the facial mask forms a barrier surrounding the wearer's mouth and nose. However, while any type of facial covering reduces the rate of pathogen transmission, the efficacy of facial masks varies depending on the fabric, the spaces between fibers, the fit of the mask against the user's face, and other similar factors. Moreover, while a facial mask may filter pathogens from transmission, pathogen particles can reside on an outer surface of the facial mask. As such, if the wearer does not take care when removing or applying the facial mask, the wearer can expose himself or herself to particles trapped on the surface of the facial mask. Typical facial masks act as buffers between the wearer and airborne particles; however, such facial masks do not act to remove or deactivate pathogen particles. Attempts have been made to create ultraviolet or electrically charged facial masks to both filter and deactivate pathogen particles; however, such attempts require complicated electronics to be used in conjunction with the masks, both increasing the cost of the masks and reducing the lifespan thereof, such as by reducing the ease of washing and reusing the mask.

Accordingly, what is needed is an antiviral electrospun fiber infused with one or more surfactants and/or metal ions that can be used to reduce the spread of airborne pathogens by both filtering and deactivating pathogen particles. Moreover, what is needed is a facial mask including fibers that can be hydrated but maintain the structural integrity and surfactants/metal ions that are water soluble under high-humidity conditions, such as those associated with human breath. The surfactants/metal ions available at hydrated fiber surfaces deactivate pathogen particles. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a method of capturing and deactivating airborne pathogen particles is now met by a new, useful, and nonobvious invention.

The novel method of capturing and deactivating airborne pathogen particles includes a step of mixing together a positively charged polyelectrolyte, a negatively charged polyelectrolyte, and an amount of surfactant molecules to form a solution. The solution is electrospun into an antiviral nanofiber membrane including a plurality of fiber strands. The plurality of fiber strands are thereby infused with the amount of surfactant molecules, such that during the electrospinning step, the electrospun fibers each include the positively charged polyelectrolyte, the negatively charged polyelectrolyte, and the amount of surfactant molecules. The amount of the surfactant molecules of the antiviral nanofiber membrane are activated in the presence of water. Once activated, the amount of the surfactant molecules are configured to deactivate one or more of a plurality of particles of an airborne pathogen, such that the antiviral nanofiber membrane captures the deactivated one or more of the plurality of particles of the airborne pathogen.

In an embodiment, the method includes a step of mixing an amount of metal ion molecules with the positively charged polyelectrolyte, the negatively charged polyelectrolyte, and the amount of surfactant molecules to form the solution. The metal ion is selected from the group consisting of copper and silver. A concentration of the amount of metal ion molecules is between 0.1% and 5%.

In an embodiment, the positively charged polyelectrolyte is selected from the group consisting of poly(allylamine hydrochloride), chitosan, and poly(amine). In an embodiment, the negatively charged polyelectrolyte is selected from the group consisting of poly(acrylic acid), (polygalacturonic acid), alginic acid, and poly(methacrylic acid). For example, an embodiment of the antiviral nanofiber membrane includes poly(allylamine hydrochloride) is the positively charged polyelectrolyte and poly(acrylic acid) as the negatively charged polyelectrolyte. In an embodiment, the ratio of the negatively charged polyelectrolyte to the positively charged polyelectrolyte is between 1:1 and 13:1.

In an embodiment, the surfactant is selected from the group consisting of sodium dodecyl sulfate, ammonium lauryl sulfate, sodium lauryl, sodium lauryl ether sulfate, sodium myreth sulfate, benzalkonium chloride, cetylpyridinium chloride, benzethonium chloride, cetyl trimethylammonium bromide, and cetyl trimethylammonium chloride. A concentration of the amount of surfactant molecules is between 0.1% and 5%.

In an embodiment, the method includes a step of forming the plurality of fiber strands into a facial mask. Next, an amount of water molecules are received on an outer surface of the facial mask, such as by exposure to human breath. The water molecules thereby hydrate the fibers and activate the amount of the surfactant molecules and/or metal ions of the plurality of fiber strands. The fibers capture a plurality of particles of an airborne pathogen on the outer surface of the facial mask. The amount of the surfactant molecules and/or metal ions then deactivate one or more of the plurality of particles of the airborne pathogen.

A novel antiviral facial mask includes an outer surface opposite an inner surface. The inner surface is configured to conform to a shape of a wearer's face. An antiviral membrane layer is disposed between the outer surface and the inner surface, with the antiviral membrane layer including a plurality of fiber strands comprised of a mixture of a positively charged polyelectrolyte, a negatively charged polyelectrolyte, and an amount of surfactant molecules. The amount of the surfactant molecules of the antiviral membrane layer are activated in the presence of water. Once activated, the amount of the surfactant molecules are configured to deactivate one or more of a plurality of particles of an airborne pathogen, such that the antiviral membrane layer captures the deactivated one or more of the plurality of particles of the airborne pathogen prior to the particles reaching the inner surface of the antiviral facial mask.

An object of the invention is to provide efficient and cost-effective facial masks capable of continuous use that not only filter pathogen particles, but also deactivate pathogen particles, without breaking down in the presence of water molecules or high humidity conditions.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1A:
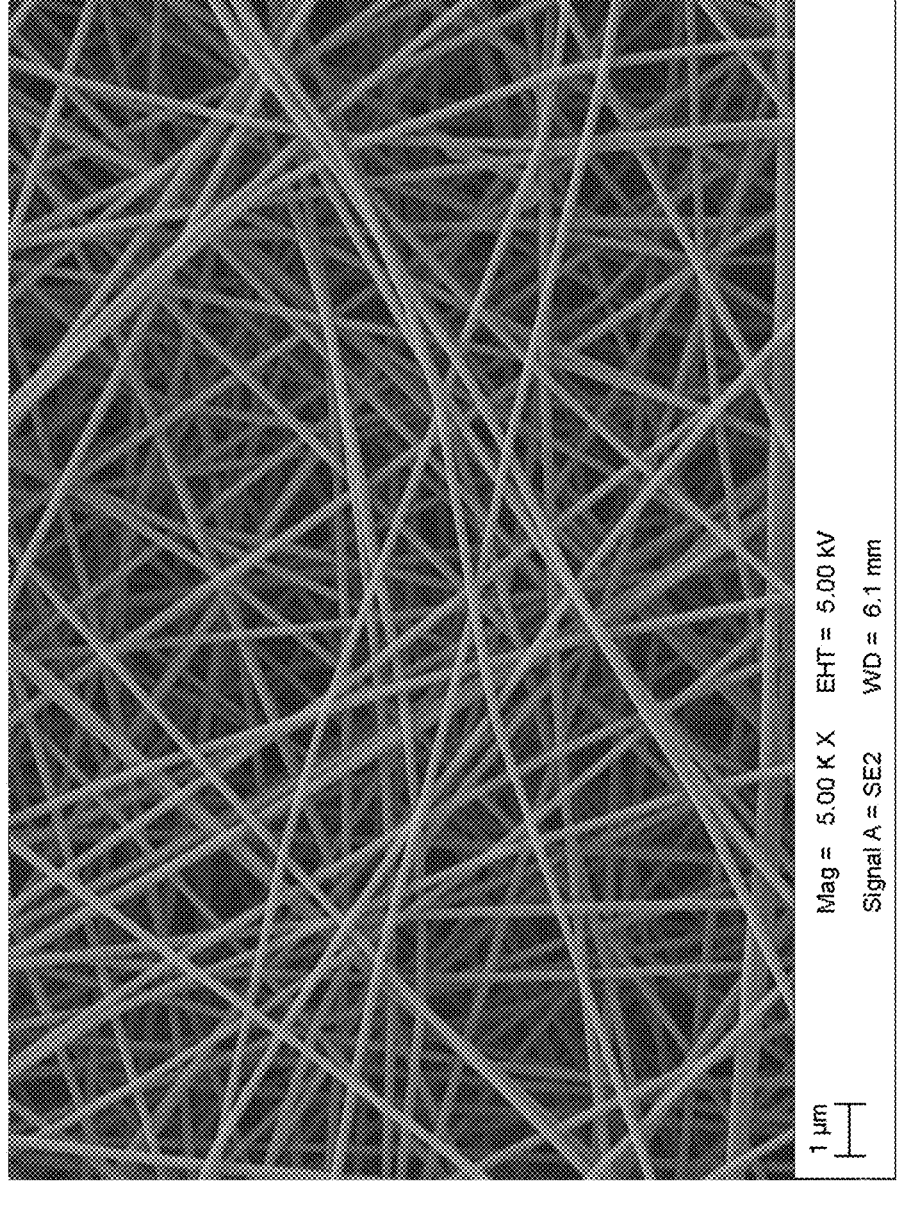
FIG. 1A is a scanning electron microscopic (SEM) image of a layer of antiviral electrospun fibers, in accordance with an embodiment of the present invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The phrases "in embodiments," "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

All numerical designations, including ranges, are approximations which are varied up or down by increments of 1.0 or 0.1, as appropriate. It is to be understood, even if it is not always explicitly stated that all numerical designations are preceded by the term "about" or "approximately." As used herein, the terms "about" or "approximately" refer to being within an acceptable error range for the particular value as determined by one of ordinary skill in the art, which will depend in part on how the value is measured or determined. As used herein, the terms "about" or "approximately" refer to ±10% of the numerical; it should be understood that a numerical including an associated range with a lower boundary of greater than zero must be a non-zero numerical, and the terms "about" and "approximately" should be understood to include only non-zero values in such scenarios.

The present invention includes methods of forming an antiviral facial mask that is capable of not only filtering pathogen particles, but also deactivating pathogen particles prior to exposure by the wearer. Typical facial masks do not deactivate pathogen particles, but rather capture at least some of the particles prior to interacting with the mask wearer. As such, the mask wearer is still prone to exposure to the pathogen particles each time the wearer interacts with the mask, such as via removal or application of the mask during daily use.

However, the present invention includes methods of deactivating pathogen particles that are filtered by and disposed on a surface of the mask by infusing one or more surfactants/metal ions within the fibers on the mask. In addition, the present invention includes methods of ensuring that the surfactant-infused fibers are non-water soluble in high-humidity conditions, such as those associated with typical human breath. Attempts have been made to form mask membranes using single-component and traditional polymers, such as polyethylene and polyester. However, these single-component membranes are not soluble in water and are not able to incorporate surfactants and metal ions in their fibers. While such membranes have been known to include polyacrylic acid, surfactants, and metal ions on the fiber surfaces, the low amount of active materials on the surface are not efficient at deactivating pathogens.

Moreover, specifically relating to particles such as those associated with SARS-CoV-2, certain infectious particles enter into human or animal cells through outer extensions, such as spike proteins, which penetrate through outer cell membranes to attach to the human or animal cells. The infectious particles are typically protected through a lipid membrane, envelope proteins, or other outer membranes that encase the nuclear proteins within each particle. However, surfactants, such as soap, include opposing ends that are hydrophilic at a first end to bond with water, and hydrophobic at the opposing end to bond with oils and fat. As such, surfactants function to denature lipid membranes of cells, such as viral particles, through the insertion of the hydrophobic tails of the surfactant into the membranes. In addition, surfactants typically form micelles that surround and encase external particles therein, with the hydrophobic ends of each molecule interacting with the viral particles, and with the hydrophilic ends of each molecule interacting with external water to be removed from an environment after being deactivated.

Accordingly, the present invention improves upon prior attempts at providing antiviral fibers by increasing the efficacy and lifespan of each mask, while simultaneously reducing complexities of assembly and use.

Figure 1B:
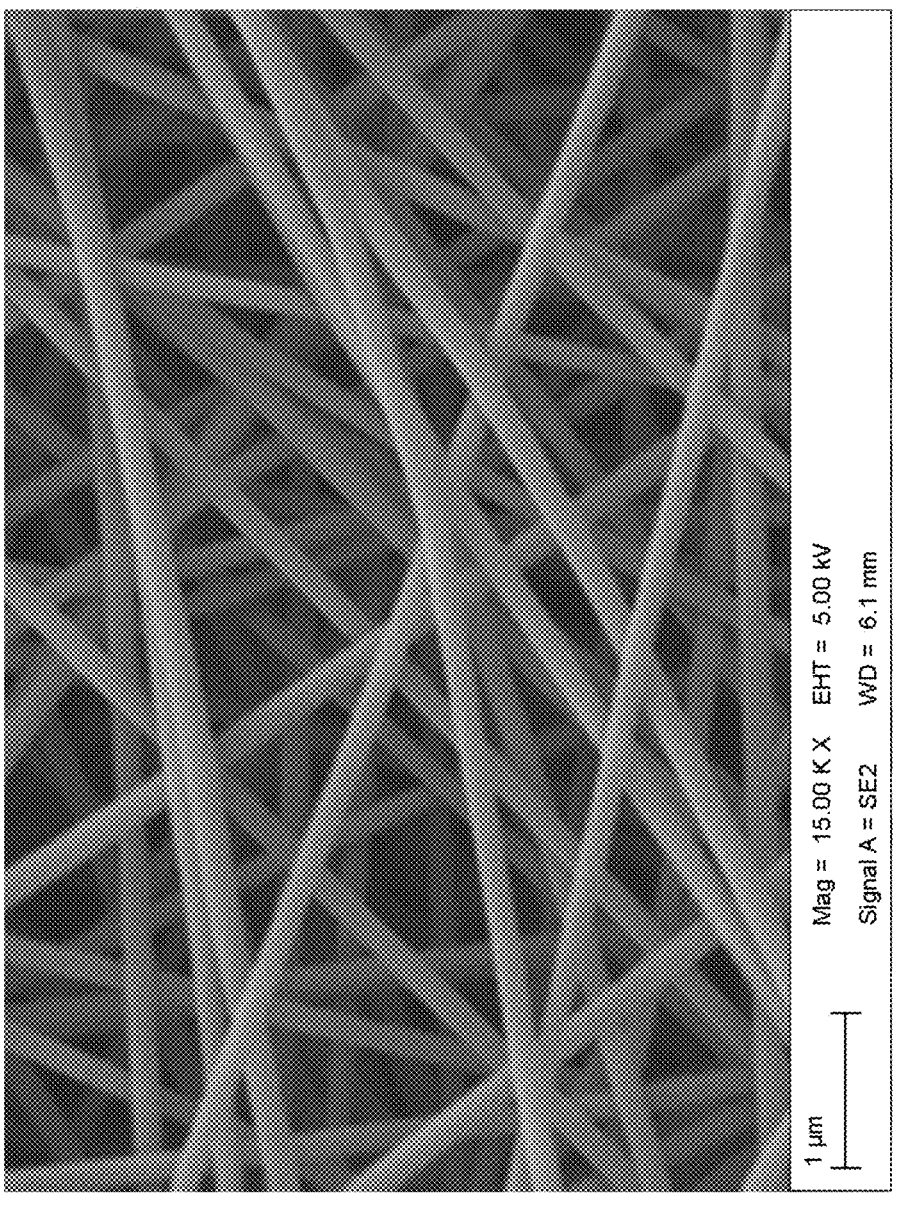
FIG. 1B is an enhanced SEM image of the layer of antiviral electrospun fibers shown in FIG. 1A.
Figure 1C:
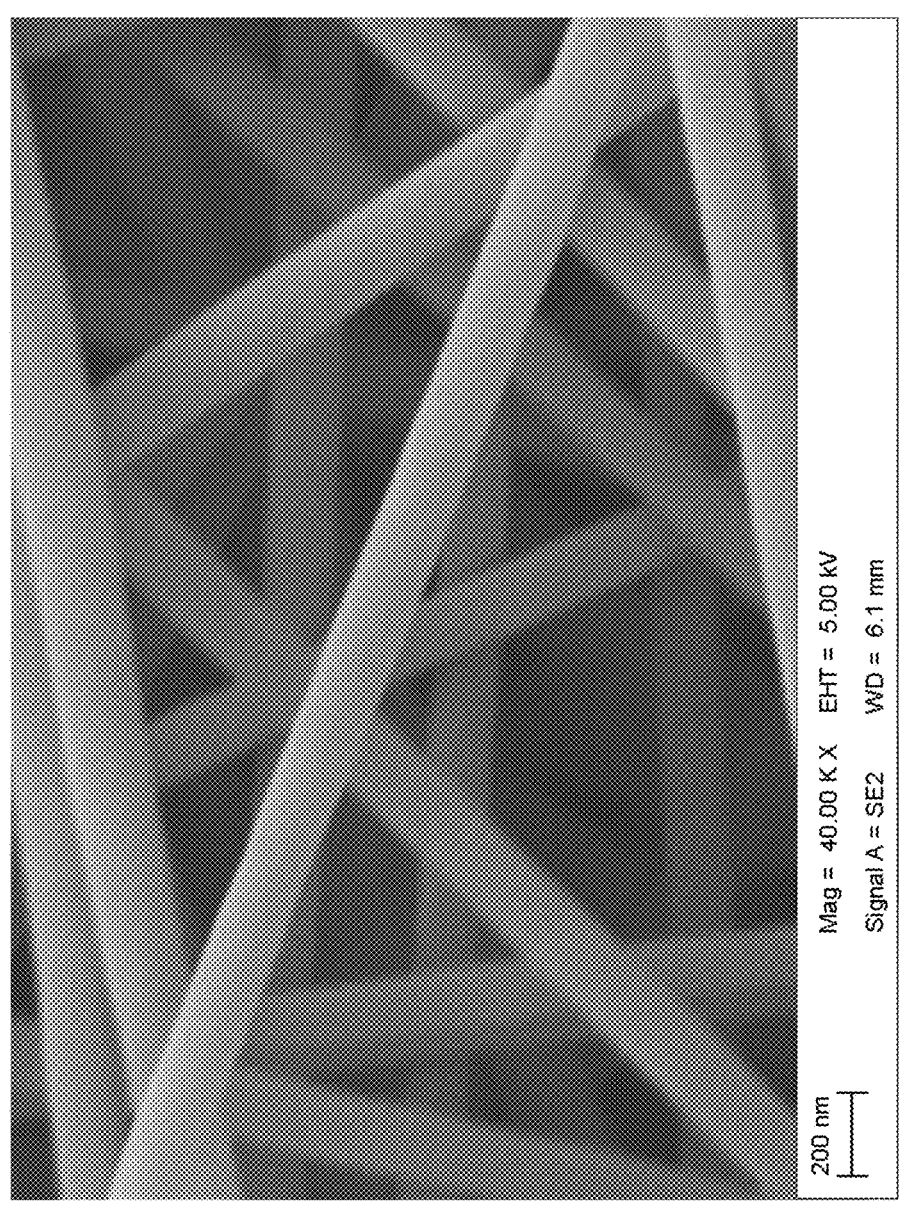
FIG. 1C an enhanced SEM image of the layer of antiviral electrospun fibers shown in FIG. 1B.

Examples of antiviral fibers are shown in FIGS. 1A-1C, which are SEM images depicting a layer of a hydrophilic nanofiber membrane with surfactants integrated therein. The nanofibers of the membrane are arranged such that small size aerosol particles (such as particles having a diameter of at least 200 nm) are incapable of passing through the nanofiber arrangement, thereby preventing a user from interacting with the blocked aerosol particles. The nanofiber membrane is composed of multiple polyelectrolytes that have opposing charges, such that the polyelectrolytes bind together in the synthesis of the nanofiber membrane.

Importantly, and in contrast to prior art attempts, multiple polyelectrolytes are employed as opposed to a single compound, and, as noted above, the polyelectrolytes are oppositely charged. In an embodiment, poly(acrylic acid) and poly(allylamine hydrochloride) are the oppositely-charged polyelectrolytes used in the synthesis of the fiber membrane (as will be described in greater detail below), with the poly(acrylic acid) polyelectrolytes being negatively charged and the poly(allylamine hydrochloride) polyelectrolytes being positively charged. However, it should be appreciated that other polyelectrolytes having opposite charges may be used, so long as one of the polyelectrolytes is positively charged and the opposing polyelectrolyte is negatively charged. Examples of positively charged polyelectrolytes include poly(allylamine hydrochloride) (described above), chitosan, and poly(amine); examples of negatively charged polyelectrolytes includes poly(acrylic acid) (described above), (polygalacturonic acid), alginic acid, and poly(methacrylic acid). In embodiments, the ratio between the concentrations of the negatively charged polyelectrolyte (such as poly(acrylic acid)) and the positively charged polyelectrolyte (such as poly(allylamine hydrochloride)) ranges from approximately 1:1 to 13:1.

In addition, an amount of a surfactant is included in the nanofiber membrane, integrated into the nanofibers during the synthesis of the membrane. In an embodiment, the surfactant is 0.1-5% sodium dodecyl sulfate; however, it should be appreciated that other surfactants can be used in combination with the polyelectrolytes to form the nanofiber membrane. Examples of surfactants include sodium dodecyl sulfate (described above), ammonium lauryl sulfate, sodium lauryl and the related alkyl-ether sulfates sodium lauryl ether sulfate (SLES), sodium myreth sulfate, benzalkonium chloride (BAC), cetylpyridinium chloride (CPC), benzethonium chloride (BZT), cetyl trimethylammonium bromide (CTAB), and cetyl trimethylammonium chloride (CTAC). In embodiments, the concentration of the surfactant in the nanofiber membrane is between approximately 0.1% and 5%. Similarly, in embodiments, the nanofiber membrane includes a concentration of metal ions of between approximately 0.1% and 5%. Examples of metal ions included in the nanofiber membrane include copper and silver ions.

Figure 2:
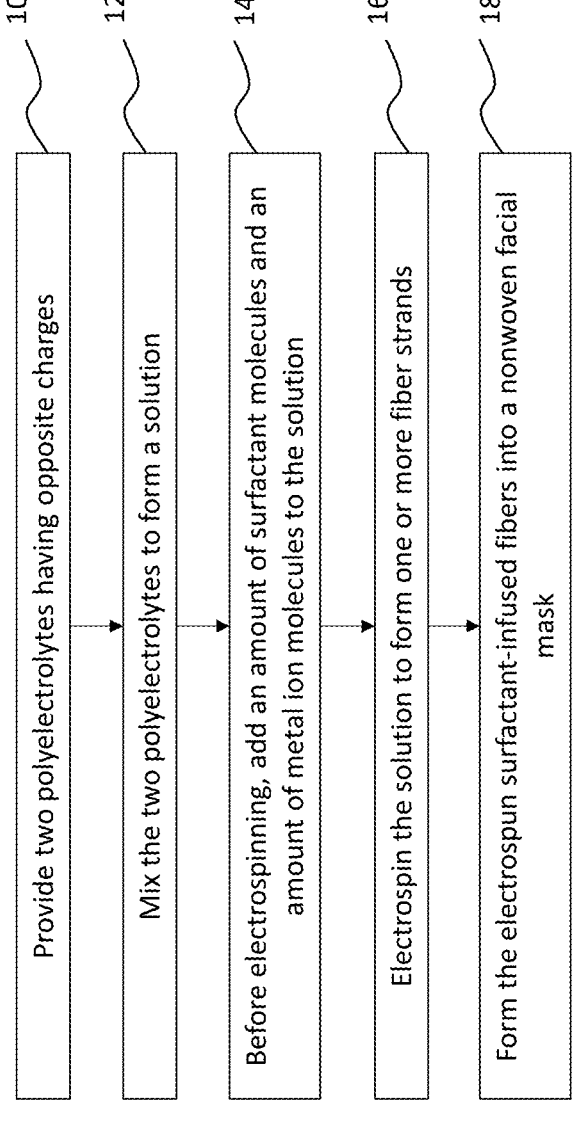
FIG. 2 is a process flow diagram depicting a method of forming an enhanced facial mask for use in the filtration and deactivation of airborne pathogen particles, in accordance with an embodiment of the present invention.
Figure 3:
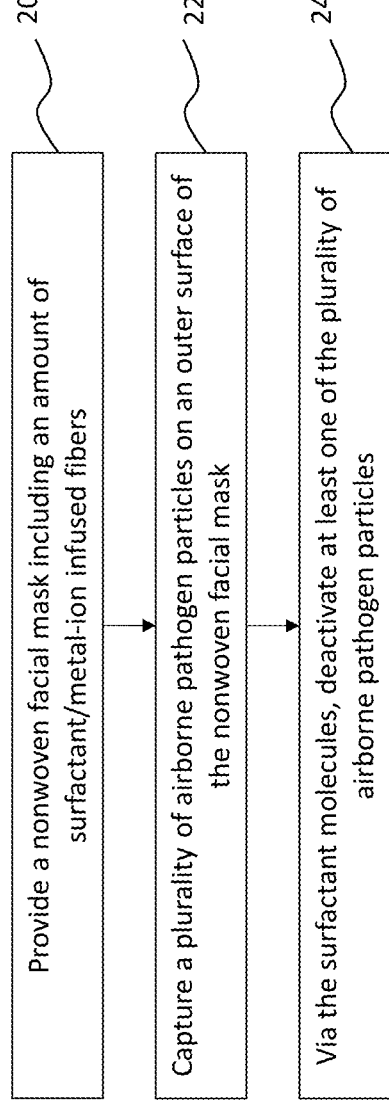
FIG. 3 is a process flow diagram depicting a method of capturing and deactivating an airborne pathogen particle, in accordance with an embodiment of the present invention.

FIGS. 2-3, in conjunction with FIGS. 1A-1C, depict process flow diagrams of a method of forming a surfactant-infused antiviral mask, and a method of deactivating airborne pathogen particles, respectively. The steps depicted in each of FIGS. 2-3 are exemplary of the methods described above; however, it should be appreciated that the steps may be performed in alternative orders and may include fewer or greater steps than those depicted in the figures.

As shown in FIG. 2, the method begins at step 10 which includes providing two polyelectrolytes having opposite charges from each other. For example, the two polyelectrolytes may be poly(acrylic acid) and poly(allylamine hydrochloride); however, it should be appreciated that other polyelectrolytes having opposite charges may be used during step 10. As noted above, in contrast to prior art attempts, multiple polyelectrolytes are employed as opposed to a single compound, and the polyelectrolytes are oppositely charged such that they can be combined. As such, during step 12, the two polyelectrolytes are mixed to form a solution.

During step 14, prior to electrospinning the solution to form fibers, an amount of surfactant molecules (such as sodium dodecyl sulfate) and an amount of metal ion molecules are added to the solution. Next, during step 16, the solution, including the two oppositely charged polyelectrolytes, the surfactant, and the metal ion molecules, is electrospun into one or more fiber strands. As such, the two oppositely charged polyelectrolytes, the surfactant molecules, and the metal ion molecules are electrospun into an amount of fiber strands that are usable in facial masks and other fiber-based applications. Importantly, the surfactant molecules and the metal ion molecules are added to the oppositely charged polyelectrolytes prior to electrospinning, such that surfactants and metal ions are embedded in whole fibers as opposed to adding the surfactant and metal ions on the fiber surfaces. As such, the method increases the amount of surfactant and metal ion molecules on each fiber, such that each fiber strand directly interacts with each of the surfactant and the metal ions during formation.

The resulting surfactant-infused fibers are stable under high-humidity conditions, including in the presence of water, because the fiber structure includes oppositely charged polyelectrolytes that strengthens the bonds within the fiber. The surfactant-infused fibers are formed into a facial mask during step 18. The fiber stability can be further improved, if necessary, by thermally crosslinking fibers together by heating at a high temperature, such as approximately 100° C. The resulting facial mask is usable to both capture and deactivate airborne pathogen particles due to the complexion of the fiber strands, as will be described in greater detail below.

As shown in FIG. 3, a method of deactivating pathogen particles begins at step 20, which includes providing a facial mask including an amount of surfactant-infused fibers as described in the sections above. The fiber is hydrophilic in nature, and the moisture from human breath hydrates the fibers and mobilizes surfactants in the fiber to interact with virus when viral particles are captured on an outer surface of the facial mask during step 22. During step 24, as surfactants interact with the virus, the hydrophobic tail of the surfactant molecules bonds to the fatty lipid membrane of viral particles, thereby allowing the hydrophilic head of the surfactant molecules to interact with the water components of the viral particles. By interacting with both the fatty lipid membrane and the water components of the viral particles, the membrane surrounding the virus denatures (such as by dissolving), thereby deactivating the viral particles on the surface of the facial mask.

Accordingly, the method of forming the antiviral mask includes mixing a solution of two oppositely charged polyelectrolytes and electrospinning the polyelectrolytes with surfactants and metal ions. The resulting fibers include strong bonds between the components, such that the fibers do not breakdown in the presence of water, as is common during high-humidity human breath. Instead, the water in human breath activates the fibers to interact with viral particles, thereby increasing the amount of particles captured and deactivated by masks made from the fibers. The resulting masks enjoy a longer lifespan than previous attempts at masks including surfactants, in addition to being simpler to manufacture and more cost effective than the complicates attempts of the prior art.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An antiviral facial mask comprising:
an outer surface;
an inner surface opposite the outer surface, the inner surface configured to conform to a shape of a wearer's face;
an antiviral membrane layer disposed between the outer surface and the inner surface, the antiviral membrane layer including:
a plurality of electrospun fiber strands comprised of a mixture of a positively charged polyelectrolyte, a negatively charged polyelectrolyte, an amount of embedded surfactant molecules, and an amount of embedded metal ion molecules, wherein the amount of embedded surfactant molecules present in the mixture is between 0.1% and 5% of the mixture;
wherein the plurality of electrospun fiber strands are thermally crosslinked by heating at approximately 100° C., whereby the plurality of electrospun fiber strands are stable in high-humidity conditions;
wherein the plurality of electrospun fiber strands block airborne aerosol particles in a submicron size range while permitting airflow associated with human breath;
wherein the amount of the embedded surfactant molecules of the antiviral membrane layer are activated upon exposure to water molecules from the human breath;
wherein, once activated and in the presence of an airborne pathogen comprising a plurality of particles having a fatty lipid membrane, on the outer layer of the antiviral facial mask, the amount of the embedded surfactant molecules interact with the fatty lipid membrane of one or more of the plurality of particles of the airborne pathogen, thereby denaturing the fatty lipid membranes of the one or more of the plurality of particles of the airborne pathogen such that the fatty lipid membranes dissolve; and
wherein the antiviral membrane layer captures and deactivates the one or more of the plurality of particles of the airborne pathogen prior to the particles reaching the inner surface of the antiviral facial mask.

2. The antiviral facial mask of claim 1, wherein the positively charged polyelectrolyte is selected from the group consisting of poly(allylamine hydrochloride), chitosan, and poly(amine), and the negatively charged polyelectrolyte is selected from the group consisting of poly(acrylic acid), (polygalacturonic acid), alginic acid, and poly(methacrylic acid).

3. The antiviral facial mask of claim 1, wherein the surfactant is selected from the group consisting of sodium dodecyl sulfate, ammonium lauryl sulfate, sodium lauryl, sodium lauryl ether sulfate, sodium myreth sulfate, benzalkonium chloride, cetylpyridinium chloride, benzethonium chloride, cetyl trimethylammonium bromide, and cetyl trimethylammonium chloride.

4. The antiviral facial mask of claim 1, wherein the airborne aerosol particles have a diameter of at least 200 nm.

* * * * *